United States Patent
Fast et al.

(10) Patent No.: US 12,372,781 B2
(45) Date of Patent: Jul. 29, 2025

(54) DEFORMABLE MEMBRANE FOR SPECKLE MITIGATION

(71) Applicant: ROCKLEY PHOTONICS LIMITED, Altrincham (GB)

(72) Inventors: Alexander Fast, Aliso Viejo, CA (US); Aaron L. Birkbeck, San Diego, CA (US); Craig Gardner, Belmont, MA (US); Haydn Frederick Jones, London (GB); Benjamin Ver Steeg, Redlands, CA (US)

(73) Assignee: Rockley Photonics Limited, Altrincham (GB)

( * ) Notice: Subject to any disclaimer, the term of this patent is extended or adjusted under 35 U.S.C. 154(b) by 185 days.

(21) Appl. No.: 18/056,678

(22) Filed: Nov. 17, 2022

(65) Prior Publication Data

US 2023/0228989 A1    Jul. 20, 2023

Related U.S. Application Data (60) Provisional application No. 63/280,993, filed on Nov. 18, 2021.

(51) Int. Cl.
*G02B 27/00* (2006.01)
*G02B 27/09* (2006.01)
*G02B 27/48* (2006.01)

(52) U.S. Cl.
CPC ..... *G02B 27/0068* (2013.01); *G02B 27/0916* (2013.01); *G02B 27/48* (2013.01)

(58) Field of Classification Search
CPC ...... A61B 5/0075; A61B 5/443; G01N 21/31; G01N 21/474; G01N 21/49; G02B 26/0858; G02B 27/0068; G02B 27/0916; G02B 27/48
See application file for complete search history.

(56) References Cited

U.S. PATENT DOCUMENTS

| | | |
|---|---|---|
| 6,517,206 B2 | 2/2003 | Shevlin |
| 6,733,132 B2 | 5/2004 | Shevlin |
| 7,866,831 B2 | 1/2011 | Kasazumi et al. |
| 8,748,806 B2 | 6/2014 | Sqalli et al. |
| 8,783,878 B2 | 7/2014 | Shevlin et al. |

(Continued)

FOREIGN PATENT DOCUMENTS

| | | |
|---|---|---|
| CN | 106773102 B | 3/2019 |
| CN | 113031255 A | 6/2021 |
| RU | 2425621 C2 | 4/2011 |
| WO | WO 2023/089129 A1 | 5/2023 |

OTHER PUBLICATIONS

Boas, D. A. et al., "Laser speckle contrast imaging in biomedical optics", Journal of Biomedical Optics, Jan. 13, 2010, vol. 15, No. 1, pp. 011109-1 through 011109-12, Society of Photo-Optical Instrumentation Engineers.

International Search Report and Written Opinion of the International Searching Authority, mailed Feb. 16, 2023, corresponding to PCT/EP2022/082481, 17 pages.

(Continued)

*Primary Examiner* — Wyatt A Stoffa
*Assistant Examiner* — Grant A Gagnon
(74) *Attorney, Agent, or Firm* — Womble Bond Dickinson (US) LLP (57) ABSTRACT

A system with a deformable membrane for speckle mitigation. In some embodiments, the system includes a laser for producing laser light; a photodetector for detecting the laser light after interaction of the laser light with a sample; and a silicon deformable membrane, for modulating the phase of the laser light.

18 Claims, 10 Drawing Sheets

(56) References Cited

U.S. PATENT DOCUMENTS

| | | |
|---|---|---|
| 10,620,447 B2 | 4/2020 | Filhaber |
| 2011/0102748 A1 | 5/2011 | Shevlin et al. |
| 2012/0206782 A1 | 8/2012 | Chan et al. |
| 2012/0206784 A1 | 8/2012 | Chan et al. |
| 2016/0054577 A1 | 2/2016 | Kilcher et al. |
| 2018/0210224 A1 | 7/2018 | Kilcher et al. |
| 2018/0292262 A1 | 10/2018 | Furstenberg et al. |

OTHER PUBLICATIONS

Ortega-Martinez, A. et al., "Contribution of speckle noise in near-infrared spectroscopy measurements", Journal of Biomedical Optics, Oct. 30, 2019, pp. 105003-1 through 105003-6, vol. 24, No. 10, Society of Photo-Optical Instrumentation Engineers.

Qureshi, M. M. et al., "In vivo study of optical speckle decorrelation time across depths in the mouse brain", Biomedical Optics Express, Nov. 1, 2017, pp. 4855-4864, vol. 8, No. 11, Optical Society of America.

Shevlin, F. et al., "Phase randomization for spatiotemporal averaging of unwanted interference effects arising from coherence", Applied Optics, Aug. 1, 2018, pages E6-E10, vol. 57, No. 22, Optical Society of America.

Shevlin, F., "A Compact, Low Cost, Phase Randomizing Device for Laser Illuminated Displays", $21^{st}$ International Display Workshops, Dec. 3, 2014, 2 pages, Society for Information Display.

PCT Third Party Observation, by Fergal Shevlin, mailed Aug. 29, 2023, corresponding to PCT/EP2022/082481, 2 pages.

DEFORMABLE MEMBRANE FOR SPECKLE MITIGATION

CROSS-REFERENCE TO RELATED APPLICATION(S)

The present application claims priority to and the benefit of U.S. Provisional Application No. 63/280,993, filed Nov. 18, 2021, entitled "DEFORMABLE MEMBRANE REFLECTOR", the entire content of which is incorporated herein by reference.

FIELD

One or more aspects of embodiments according to the present disclosure relate to speckle mitigation, and more particularly to a deformable membrane for speckle mitigation.

BACKGROUND

Speckle may be an important source of error in a sensing system employing a coherent light source. For example, in a spectrophotometer used to determine the extent to which various constituents may be present in a sample, speckle may affect the signal to noise ratio at the photodetector receiver of the spectrophotometer, and thereby introduce measurement errors.

It is with respect to this general technical environment that aspects of the present disclosure are related.

SUMMARY

According to an embodiment of the present disclosure, there is provided a system, including: a laser for producing laser light; a photodetector for detecting the laser light after interaction of the laser light with a sample; and a silicon deformable membrane, for modulating the phase of the laser light.

In some embodiments, the silicon deformable membrane is configured to modulate the phase of the laser light before the interaction of the laser light with the sample.

In some embodiments, the silicon deformable membrane is configured to modulate the phase of the laser light after the interaction of the laser light with the sample.

In some embodiments, the system is configured to cause the laser light to reflect from the silicon deformable membrane.

In some embodiments, the system is configured to cause the laser light to be transmitted through the silicon deformable membrane.

In some embodiments, the silicon deformable membrane has a thickness of at least 0.5 microns.

In some embodiments, the silicon deformable membrane has a thickness of at most 5 microns.

In some embodiments, the system further includes a membrane frame supporting the silicon deformable membrane.

In some embodiments, the membrane frame has a thickness at least twice a thickness of the silicon deformable membrane.

In some embodiments, the membrane frame has a thickness at most 50 times the thickness of the silicon deformable membrane.

In some embodiments, the membrane frame surrounds the silicon deformable membrane.

In some embodiments, the system further includes a transition region inside the membrane frame and surrounding the silicon deformable membrane, the transition region having a thickness greater than that of the silicon deformable membrane and less than that of the membrane frame.

In some embodiments, the perimeter of the silicon deformable membrane has a curvilinear shape.

In some embodiments, the system further includes an actuator frame supporting the membrane frame.

In some embodiments, the actuator frame has a thickness of at least 50 microns.

In some embodiments, the system further includes a piezoelectric actuator coupled to the silicon deformable membrane.

In some embodiments, the piezoelectric actuator is a cantilevered piezoelectric actuator.

In some embodiments, the piezoelectric actuator is monolithically integrated with the actuator frame, the membrane frame, and the silicon deformable membrane.

In some embodiments, the piezoelectric actuator is on a shelf at one end of the actuator frame, and the shelf is connected to the membrane frame by a first tab.

In some embodiments, the silicon deformable membrane is connected to the actuator frame by a second tab, opposite the first tab.

In some embodiments, the piezoelectric actuator has a resonant mode extending over a range of frequencies, and the silicon deformable membrane has two resonant modes within the range of frequencies.

BRIEF DESCRIPTION OF THE DRAWINGS

These and other features and advantages of the present disclosure will be appreciated and understood with reference to the specification, claims, and appended drawings wherein:

DETAILED DESCRIPTION

The detailed description set forth below in connection with the appended drawings is intended as a description of exemplary embodiments of a deformable membrane for speckle mitigation provided in accordance with the present disclosure and is not intended to represent the only forms in which the present disclosure may be constructed or utilized. The description sets forth the features of the present disclosure in connection with the illustrated embodiments. It is to be understood, however, that the same or equivalent functions and structures may be accomplished by different embodiments that are also intended to be encompassed within the scope of the disclosure. As denoted elsewhere herein, like element numbers are intended to indicate like elements or features.

In a spectrophotometer used to analyze the composition of a sample, light, at various wavelengths, from a light source 105, may illuminate the sample, and the light may eventually propagate to a photodetector 115, after scattering from the surface or the interior of the sample, or propagating through a portion of the sample, or undergoing a combination of such processes. The properties of the sample may affect the proportion of the light from the light source that reaches the photodetector; for example, if the sample absorbs light strongly at a first wavelength and weakly at a second wavelength, a greater proportion of the light from the light source may reach the detector at the second wavelength than at the first wavelength. Different chemical constituents in the sample may have different absorption spectra; as such, the spectral response of the sample may be measured and used to infer aspects of the chemical composition of the sample. If the sample is the tissue of a patient, or "subject" (e.g., if it is a portion of the skin and subcutaneous tissue just beneath the skin), the spectral response may be used to infer the extent to which various constituents (e.g., water or glucose) are present in the tissue.

Figure 1:
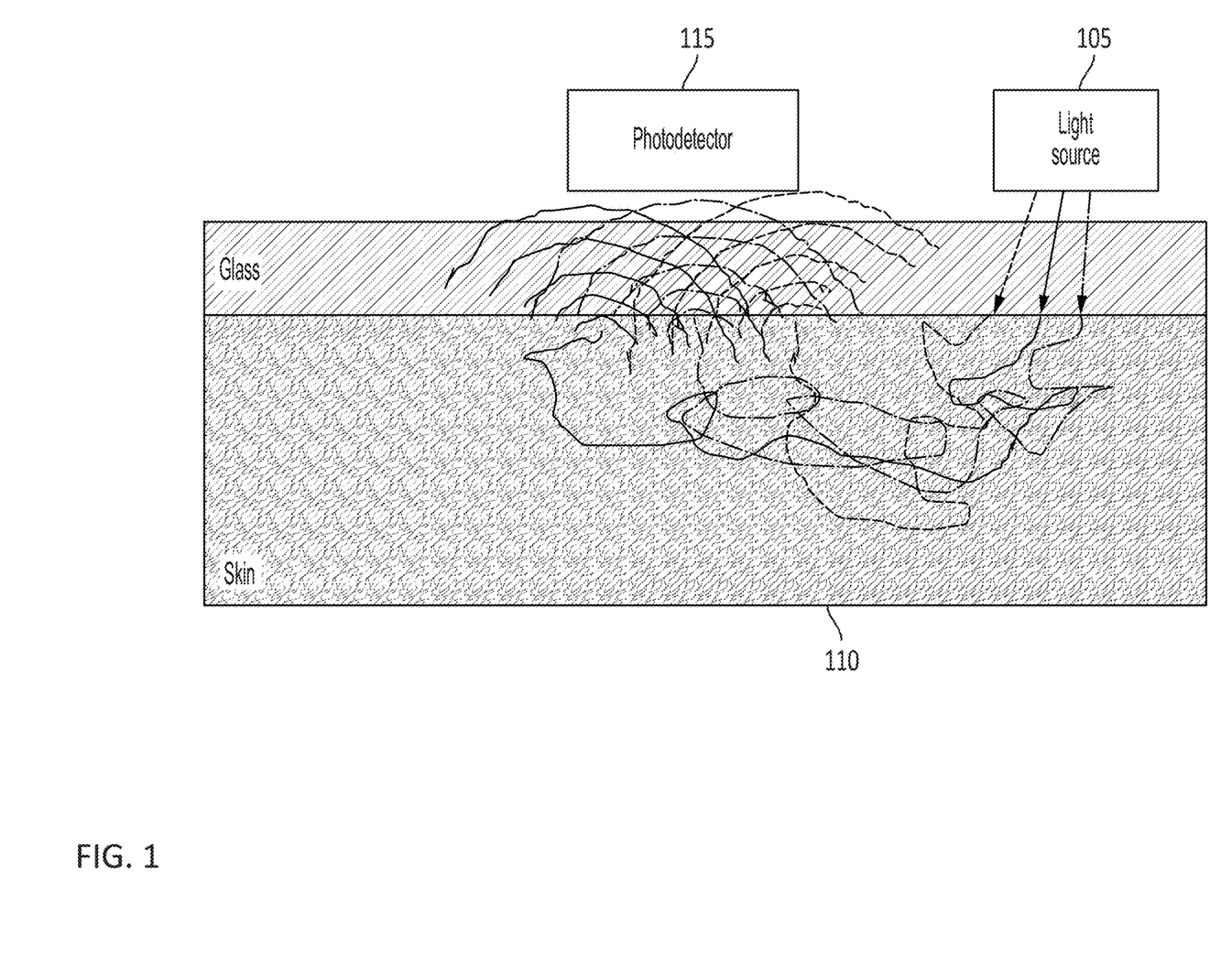
FIG. 1 is a block diagram of a spectrophotometer and a sample, according to an embodiment of the present disclosure.

If the light source is a coherent light source (e.g., a laser), then, as illustrated in FIG. 1, constructive or destructive interference may occur between components of the light taking different paths from the lights source to the photodetector. This effect, which may be referred to as "speckle" may be a source or error in the measurement of the spectral response.

Figure 2A:
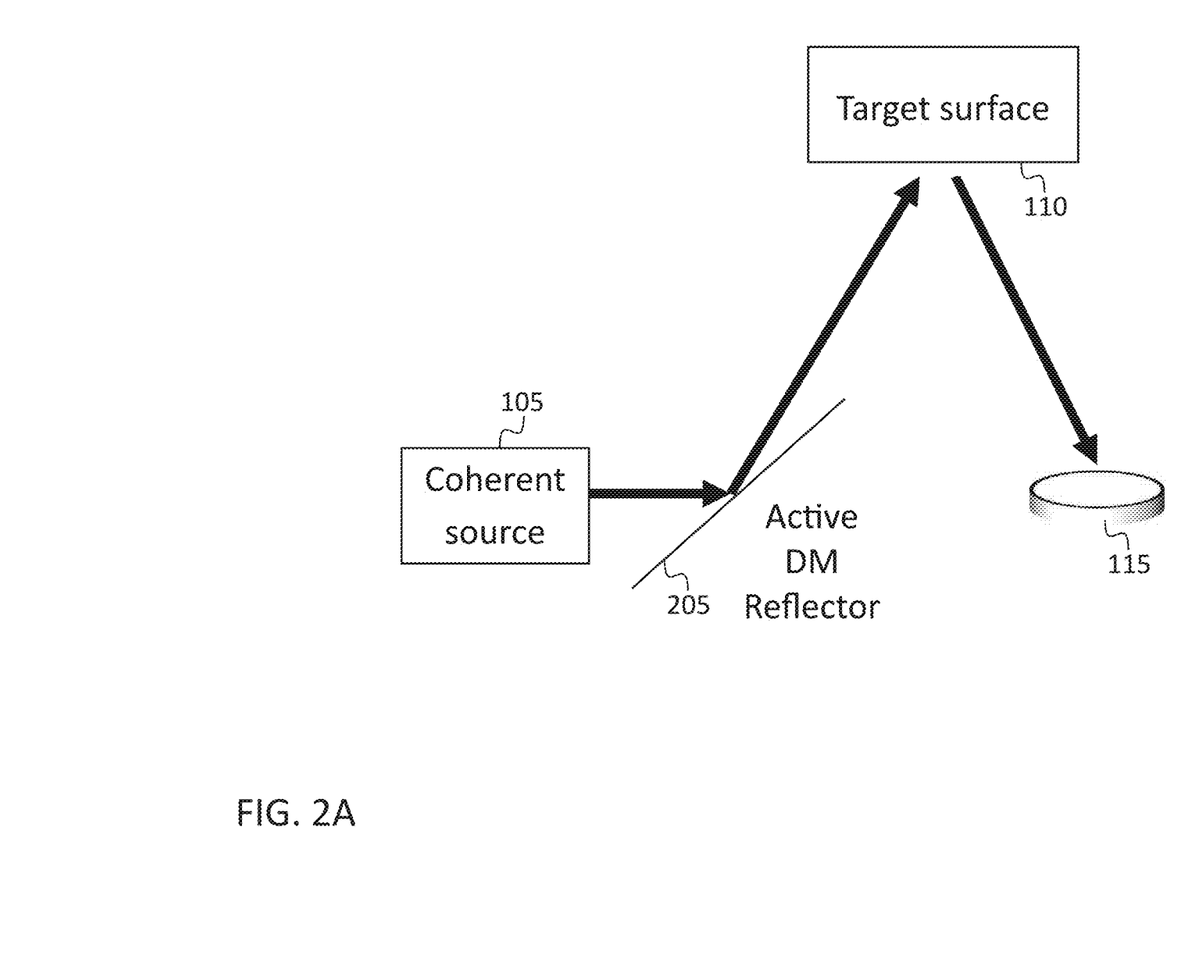
FIG. 2A is a block diagram of a spectrophotometer with a system for speckle mitigation, according to an embodiment of the present disclosure.
Figure 2B:
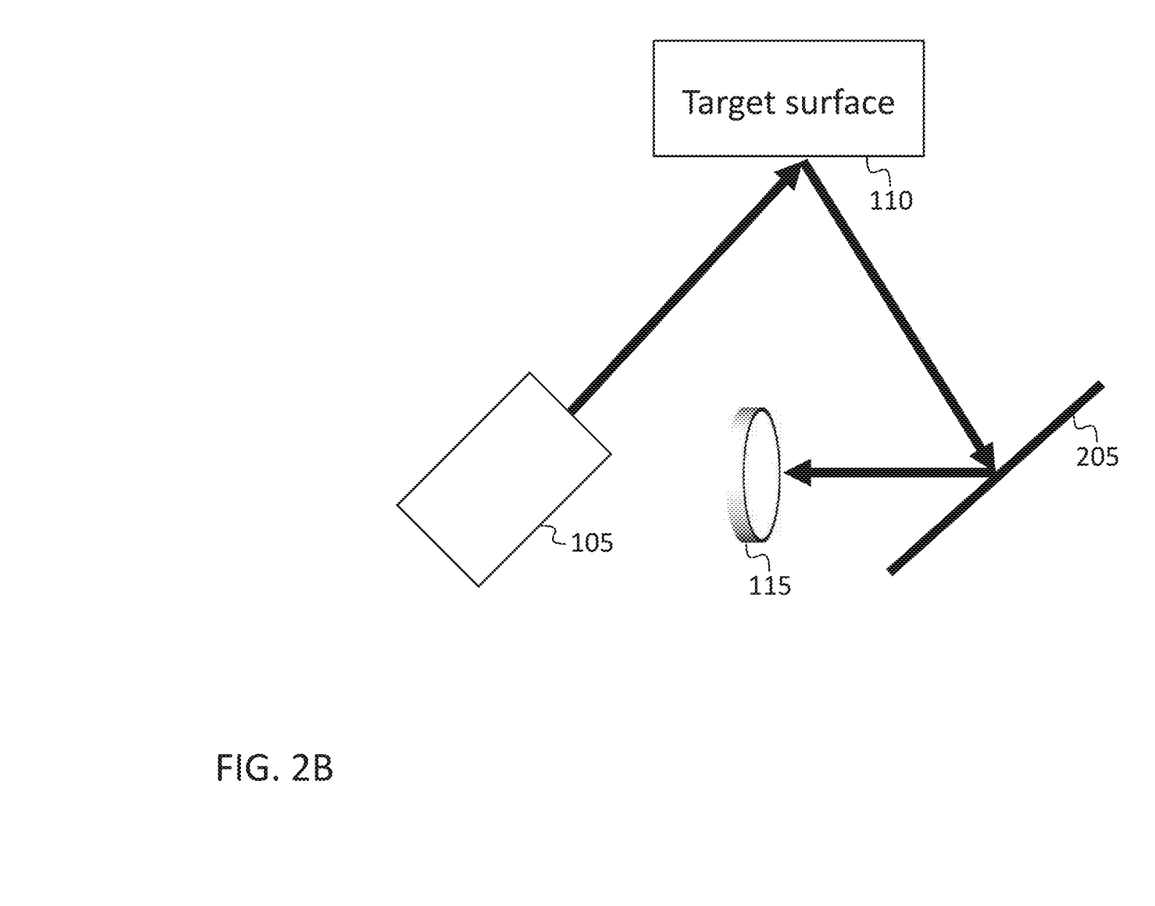
FIG. 2B is a block diagram of a spectrophotometer with a system for speckle mitigation, according to an embodiment of the present disclosure.
Figure 2C:
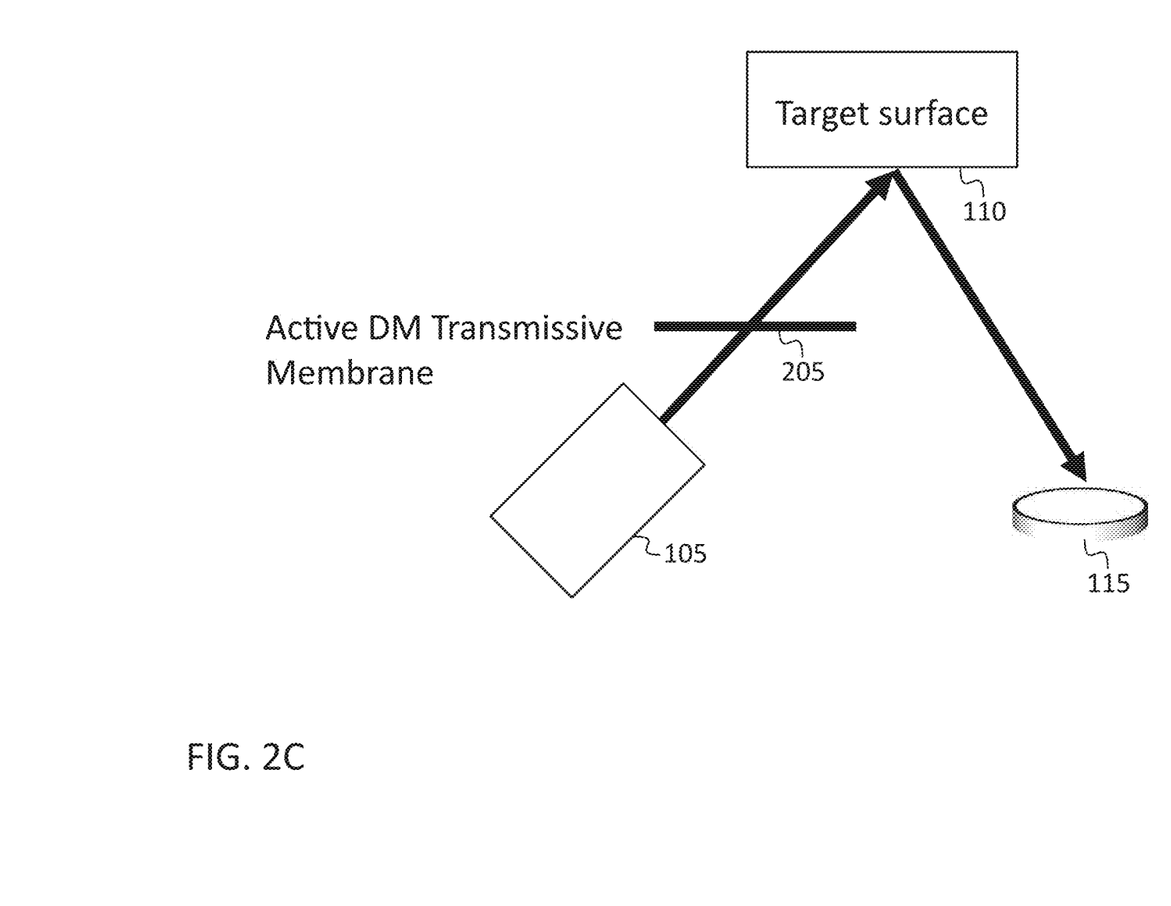
FIG. 2C is a block diagram of a spectrophotometer with a system for speckle mitigation, according to an embodiment of the present disclosure.
Figure 2D:
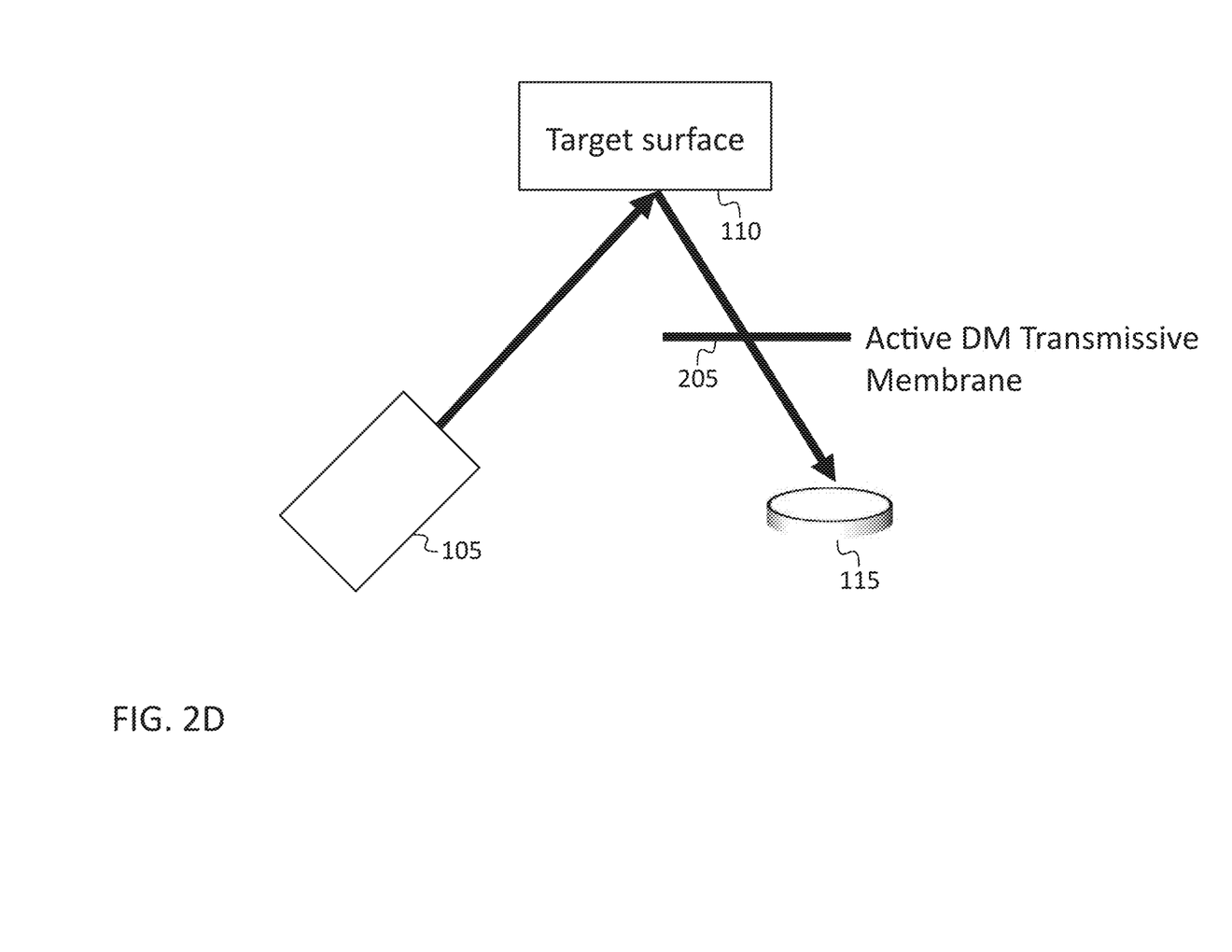
FIG. 2D is a block diagram of a spectrophotometer with a system for speckle mitigation, according to an embodiment of the present disclosure.

As such, in some embodiments, a system and method for speckle mitigation is employed to reduce the effects of speckle, by applying differential phase modulation to the different paths the light may take to the photodetector. For example, as shown in FIG. 2A, light from the light source 105 may reflect from an active deformable membrane (DM) before interacting with the sample (or "target surface") or (as illustrated in FIG. 2B), after interacting with the sample, or, as shown in FIG. 2C, the light from the light source 105 may be transmitted through an active deformable membrane before interacting with the sample or (as illustrated in FIG. 2D), after interacting with the sample. In operation, the membrane may be driven (e.g., with a suitable mechanical actuator, such as a piezoelectric actuator) to vibrate, so that its shape changes with time, and so that light reflected from (or transmitted through) the membrane undergoes a phase shift that is different for light reflected from (or transmitted through) different points on the membrane. This phase modulation may mitigate speckle because, for example, if at a first point in time (at which the membrane has a first shape) interference at the photodetector increases the total detected optical power, then at a second point in time (at which the membrane has a second shape, different from the first shape), interference at the photodetector may decrease the total detected optical power, and on average the total detected optical power may be more similar (than in the absence of speckle mitigation) to what it would be in absence of speckle.

Figure 3A:
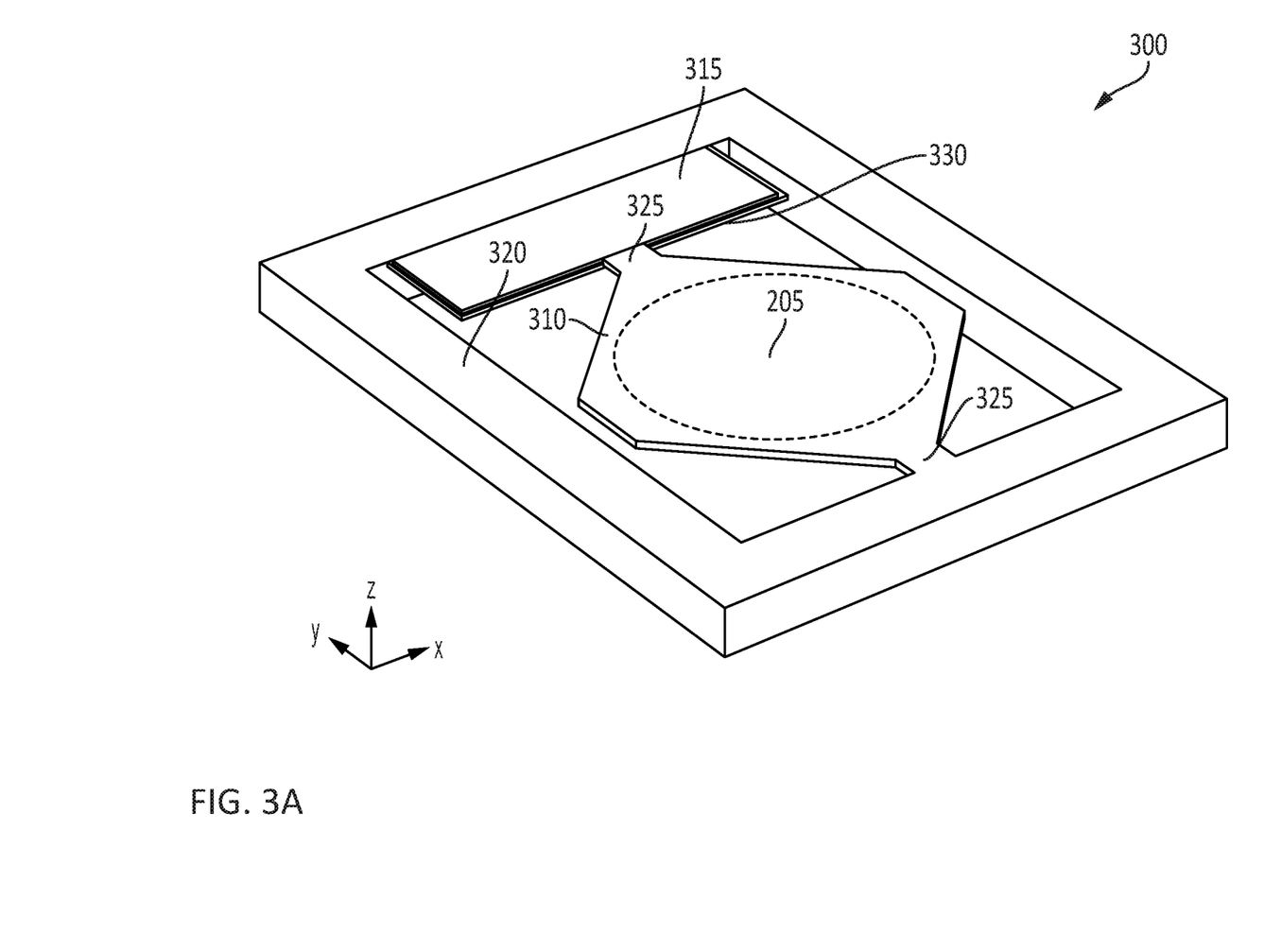
FIG. 3A is a perspective view of a phase modulator for speckle mitigation, according to an embodiment of the present disclosure.

In some embodiments, the deformable membrane is a silicon deformable membrane. FIG. 3A shows a phase modulator for speckle mitigation 300, in one embodiment. In the embodiment of FIG. 3A the deformable membrane 205 is a thin circular membrane (which may be employed as a reflector) surrounded by a thicker structure referred to herein as the membrane frame 310. The membrane frame 310 and a piezoelectric actuator 315 are surrounded by an actuator frame 320, which may operate as a rigid support for the piezoelectric actuator 315 and the membrane frame 310. The deformable membrane 205 may have a thickness between 0.5 microns and 10 microns (e.g., a thickness of about 2 microns). It may be a circular membrane, as illustrated in FIG. 3A, or its perimeter may have another curvilinear shape (e.g., an elliptical shape, or the shape of a polygon with rounded corners) or an arbitrary shape (e.g., the shape of a regular or irregular polygon). The membrane frame 310 in the embodiment of FIG. 3A is approximately square, with two corners being the points of support for the membrane frame 310. At these two corners the membrane frame 310 is supported by two tabs 325, one of which connects the membrane frame 310 to the actuator frame 320 and the other of which, at the opposite corner of the membrane frame 310, connects the membrane frame 310 to the piezoelectric actuator 315. The other two corners of the membrane frame 310 may be truncated, as shown, which may reduce the overall size of the device. The thickness of the membrane frame may be selected to be sufficiently large that the membrane frame 310 is able to anchor and constrain the edges of the deformable membrane 205, without being sufficiently large that its mass significantly diminishes the motion that the piezoelectric actuator 315 is able to impart. For example, the membrane frame 310 may have a thickness equal to at least twice the thickness of the deformable membrane 205 and at most 50 times the thickness of the deformable membrane 205. In some embodiments, the membrane frame 310 has a thickness between 4 microns and 100 microns (e.g., between 10 microns and 40 microns).

In the embodiment of FIG. 3A, the piezoelectric actuator 315 is a rectangular piezoelectric sheet on a shelf 330 that is slightly larger than the piezoelectric actuator 315. The piezoelectric actuator 315 is driven through electrodes on two surfaces of the piezoelectric actuator 315. In some embodiments, one electrode is present on each surface; in some embodiments multiple electrodes may be present on each surface, making it possible to control the electric fields applied respectively to different portions of piezoelectric actuator 315 independently. One of the electrodes may cover the upper surface of the piezoelectric actuator 315 (in the orientation shown in FIG. 3A) and the other electrode may be on the lower surface of the piezoelectric actuator 315 (e.g. on the top surface of the shelf 330). The piezoelectric actuator 315 may be constructed such that the application of a voltage across the electrodes causes the piezoelectric actuator 315 to bend about an axis parallel to the x-axis of FIG. 3A, so that the tab 325 connecting the membrane frame 310 to the piezoelectric actuator 315 is displaced upward or downward (in a direction parallel to the z axis). A piezoelectric actuator configured to deform in this manner (e.g., by bending about an axis in the plane of the (substantially planar) actuator) may be referred to as a "cantilevered" piezoelectric actuator.

The piezoelectric actuator 315 may be fabricated by depositing the piezoelectric material or materials (which may be any suitable piezoelectric material or materials, such as aluminum nitride) directly onto the shelf 330. As such, the piezoelectric actuator 315 may be integrated into the phase modulator for speckle mitigation 300, and the phase modulator for speckle mitigation 300 may be a monolithically integrated device. As used herein an "integrated", or "monolithically integrated" device is one in which the components are fabricated in place, rather than being separately fabricated and then assembled (e.g., by bonding or soldering).

In the embodiment of FIG. 3A, the overall thickness of the phase modulator for speckle mitigation 300 (which is determined by the thickest component, the actuator frame 320), may be between 50 microns and 4 mm (e.g., it may be 200 microns, as illustrated), the overall length (along the y direction) of the phase modulator for speckle mitigation 300 may be between 500 microns and 10 mm (e.g., it may be about 3 mm, as illustrated), and the overall width (along the x direction) of the phase modulator for speckle mitigation 300 may be between 300 microns and 6 mm (e.g., it may be about 2.5 mm, as illustrated). The thickness of the actuator frame 320 may be selected to provide sufficient rigidity to avoid significant loss of acoustic energy (from the piezoelectric actuator 315) via deformation of the actuator frame 320 or via leakage of acoustic energy to the structure supporting the actuator frame 320.

The phase modulator for speckle mitigation 300 may be formed, except for the piezoelectric actuator 315, from a single monolithic piece of material, e.g., by etching. For example, the phase modulator for speckle mitigation 300 of FIG. 3A may be formed from a 200 micron thick wafer of crystalline silicon by etching a rectangular pocket into the wafer to a depth such that the material remaining at the bottom of the pocket has a thickness equal to the thickness of the membrane frame 310 (which may be the same as the thickness of the shelf 330). A second, circular pocket may then be etched into the bottom of the first pocket, with a thickness at the bottom of the second pocket equal to the thickness of the deformable membrane 205, to form the circular deformable membrane 205. Another etching step may be used to remove the material around the membrane frame 310 and the shelf 330 (leaving in place the tabs 325 and leaving the shelf 330 connected, along one edge, to the actuator frame 320). The layers of the piezoelectric actuator 315 may be deposited on the shelf 330 (before or after the etching steps described above); the resulting product may be that shown in FIG. 3A (upside down, if the cavities are etched into the wafer from the top, as described above). In some embodiments, a second piezoelectric actuator 315 is formed on the other surface of the shelf 330 (e.g., on the bottom surface of the shelf 330, in the orientation of FIG. 3A).

If fabricated as described above, the boundary between the membrane frame 310 and the deformable membrane 205 may be a single step in thickness on the bottom surface of the element which includes the membrane frame 310 and the deformable membrane 205. The top surface of this element, in the embodiment of FIG. 3A, is flat. In other embodiments, there may be more than one step in thickness (e.g., the thickness may be reduced from the thickness of the membrane frame 310 to the thickness of the deformable membrane 205 in two steps (e.g., in two concentric circular steps, forming, between the two steps, a transition region having a thickness greater than that of the silicon deformable membrane and less than that of the membrane frame) or in more than two steps. In some embodiments, the deformable membrane 205 may be defined by two pockets, one on each side of the membrane frame 310 (e.g., there may be a step in thickness on the bottom surface of the element (e.g., in the orientation of FIG. 3A) and also a step in thickness on the top surface of the element (so that, unlike in the embodiment of FIG. 3A, the top surface is not flat).

The material from which the actuator frame 320, the shelf 330, the tabs 325, the membrane frame 310 and the deformable membrane 205 are formed may be any suitable material, e.g., it may be crystalline silicon, polycrystalline silicon, silicon nitride (e.g., crystalline silicon nitride), or silicon oxide (e.g., silicon dioxide, SiO2). Such a deformable membrane may be referred to as a "silicon deformable membrane". As used herein, a "silicon deformable membrane" is a deformable membrane containing at least 30 atomic percent (30 at %) silicon.

In some embodiments, the phase modulator for speckle mitigation 300 may be constructed such that a resonant mode of the piezoelectric actuator 315 is at a frequency, and has a width in frequency (e.g., it extends over a range of frequencies), such that it overlaps with the frequencies of at least two resonant modes of the deformable membrane 205. For example, the piezoelectric actuator 315 may have a resonant mode at a frequency of 50 kHz, with a quality factor (Q) of about 10, so that the resonant enhancement of the response of the piezoelectric actuator 315 (e.g., the enhancement in the displacement achieved for an electrical drive signal of a given amplitude) may extend over a range of frequencies from about 47.5 kHz to 52.5 kHz, and the deformable membrane 205 may have a resonant mode at 49 kHz and another resonant mode at 51 kHz, both of which fall within the range of frequencies over which the resonant mode of the piezoelectric actuator 315 extends (e.g. over which it exhibits a resonant response). In this case it may be possible to drive the piezoelectric actuator 315, at either of the resonant frequencies of the deformable membrane 205, with a relatively modest voltage (e.g., with a drive signal having an amplitude of 3 V, peak-to-peak) and nonetheless achieve a displacement, of points on the surface of the deformable membrane 205, sufficient to produce significant phase randomization across the membrane. For example, the peak-to-peak motion of the surface of the deformable membrane 205 may at some points be one-quarter of the wavelength of the light (e.g., at least 200 nm, e.g., between 300 nm and 600 nm), resulting in peak-to-peak phase randomization upon reflection of about one-half cycle, or the peak-to-peak motion may be about one-half wavelength (e.g., at least 400 nm, e.g., between 600 nm and 1200 nm), resulting in peak-to-peak phase modulation upon reflection of about one cycle. Motion of the membrane of this magnitude may be sufficient to achieve significant speckle noise mitigation. The maximum amplitude of the motion of the deformable membrane 205 may generally decrease (when a drive voltage having a fixed amplitude is applied to the piezoelectric actuator 315), as the frequency of the drive voltage and of the mode or modes of the deformable membrane 205 increases. In some embodiments, the frequencies of the modes (or "spatial modes") of the deformable membrane 205 that are driven are between twice and 500 times the fundamental mode of the deformable membrane 205.

In some embodiments, two or more resonant modes of the deformable membrane 205 may be driven simultaneously, so that in addition to the phase change upon reflection being imparted to the light at any point on the membrane changing with time (as the membrane deflects back and forth), the map of phase modulation amplitude across the surface of the deformable membrane 205 may change, as the modes of the membrane beat against each other. In some embodiments, this may be accomplished by driving the piezoelectric actuator 315 with two or more tones, each having a frequency equal to (or approximately equal to) the frequency of a respective one of the resonant modes of the deformable membrane 205, or by driving the piezoelectric actuator 315 with a broadband electrical signal (e.g., with a square wave), or by quickly switching between one or more frequency within the resonance bandwidth of the piezoelectric actuator 315. A square wave may be used, for example, to create time varying semi-chaotic behavior in the deformable membrane 205. A suitable drive circuit (e.g., a processing circuit (discussed in further detail below), or a processing circuit connected to an analog to digital converter or to a drive amplifier) may be used to drive the piezoelectric actuator 315. The output impedance of the drive circuit may affect the quality factor of the resonant modes of the piezoelectric actuator 315; in some embodiments the output impedance is less than 1 kOhm.

Figure 3B:
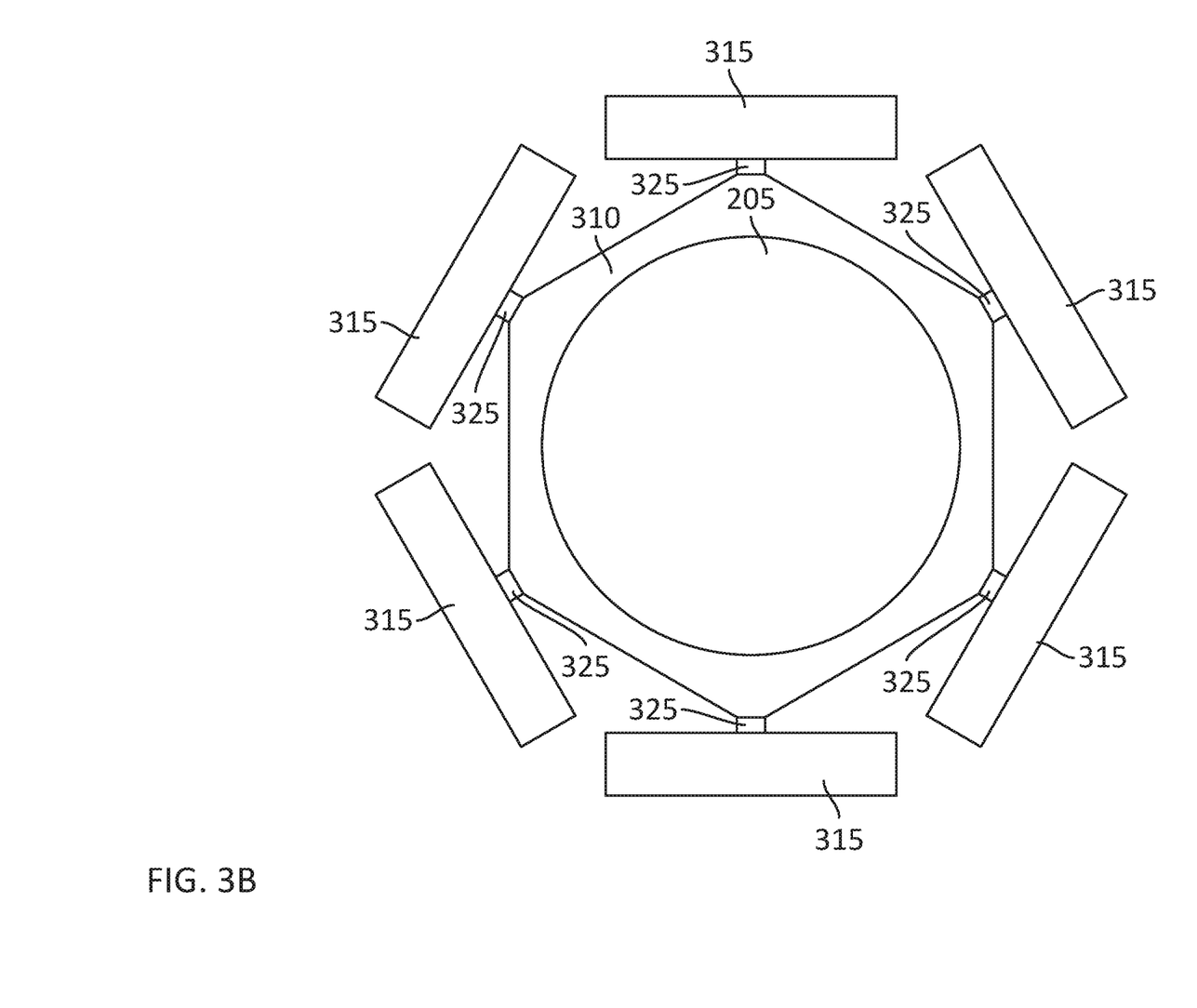
FIG. 3B is a plan view of a portion of a phase modulator for speckle mitigation, according to an embodiment of the present disclosure.
Figure 3C:
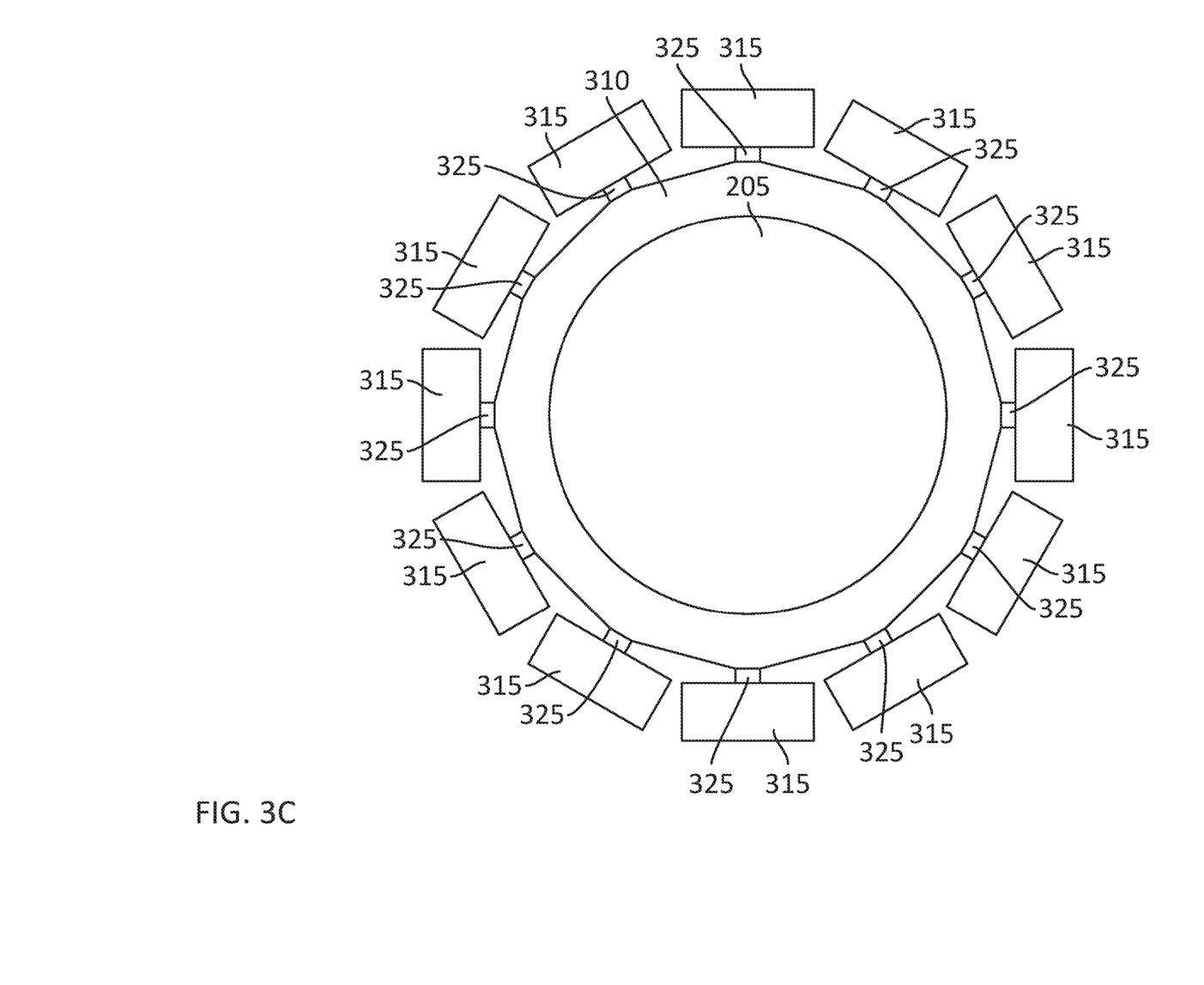
FIG. 3C is a plan view of a portion of a phase modulator for speckle mitigation, according to an embodiment of the present disclosure.

In some embodiments the phase modulator for speckle mitigation 300 includes more than one piezoelectric actuator 315. For example, in the embodiment of FIG. 3A, the corner supported by a tab directly connected to the actuator frame 320 may instead be supported by a second piezoelectric actuator 315, so that the membrane frame 310 is supported at two opposite corners by two respective piezoelectric actuators 315. In other embodiments each of the four corners of a square membrane frame 310 may be supported by a respective piezoelectric actuator 315, or each of (or each of some of) the corners (e.g., every other corner) of a different shape (e.g., of a regular (or irregular) polygon (e.g., a triangle, a hexagon (as shown in FIG. 3B), an octagon, or a dodecagon (as shown in FIG. 3C) may be supported by a respective piezoelectric actuator 315. In such embodiments some or all of the piezoelectric actuators 315 may be supported by a suitably-shaped (e.g., polygonal) actuator frame 320 (not shown in FIGS. 3B and 3C).

Figure 4A:
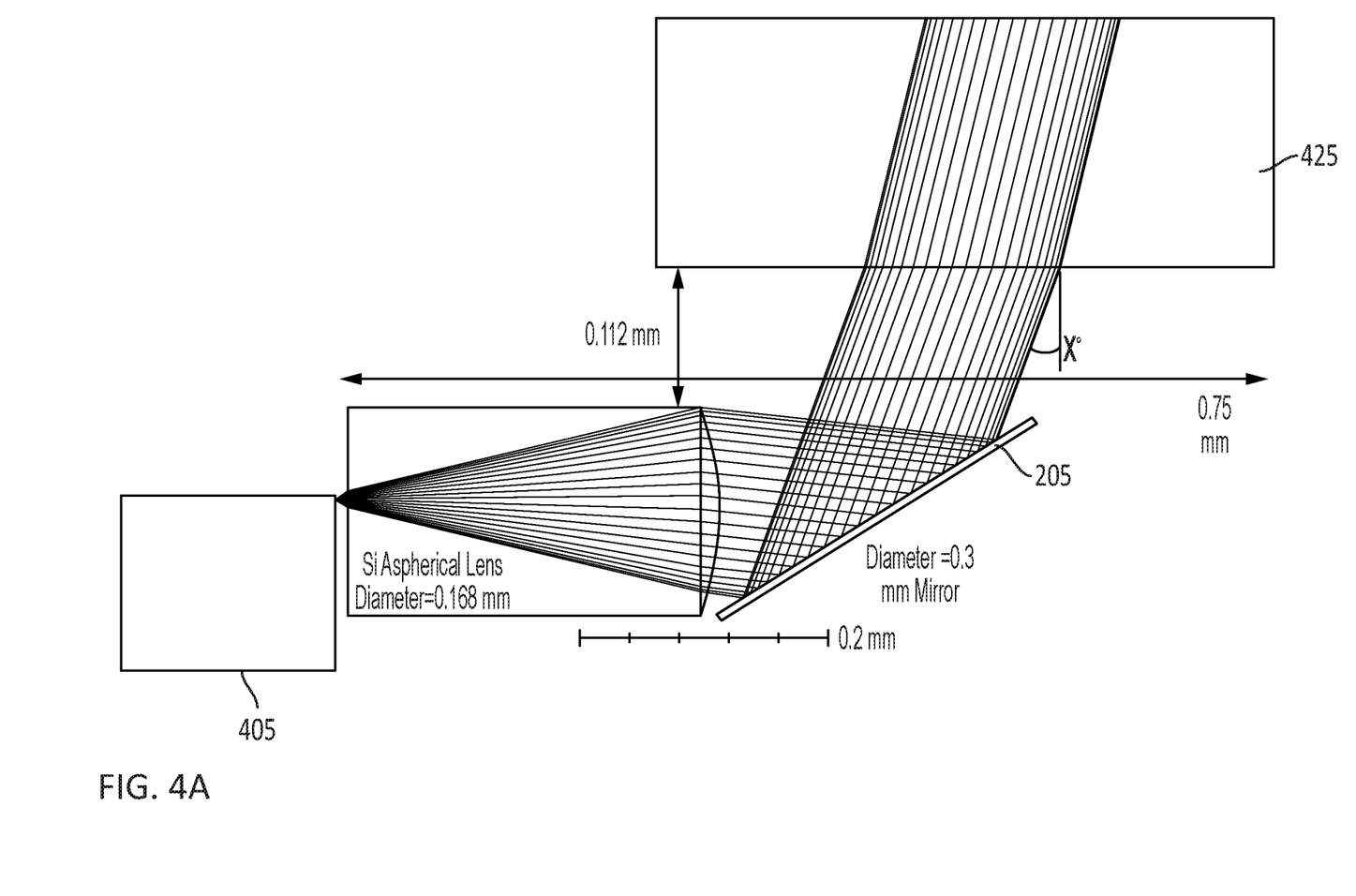
FIG. 4A is a side view of a portion of a spectrophotometer, according to an embodiment of the present disclosure.
Figure 4B:
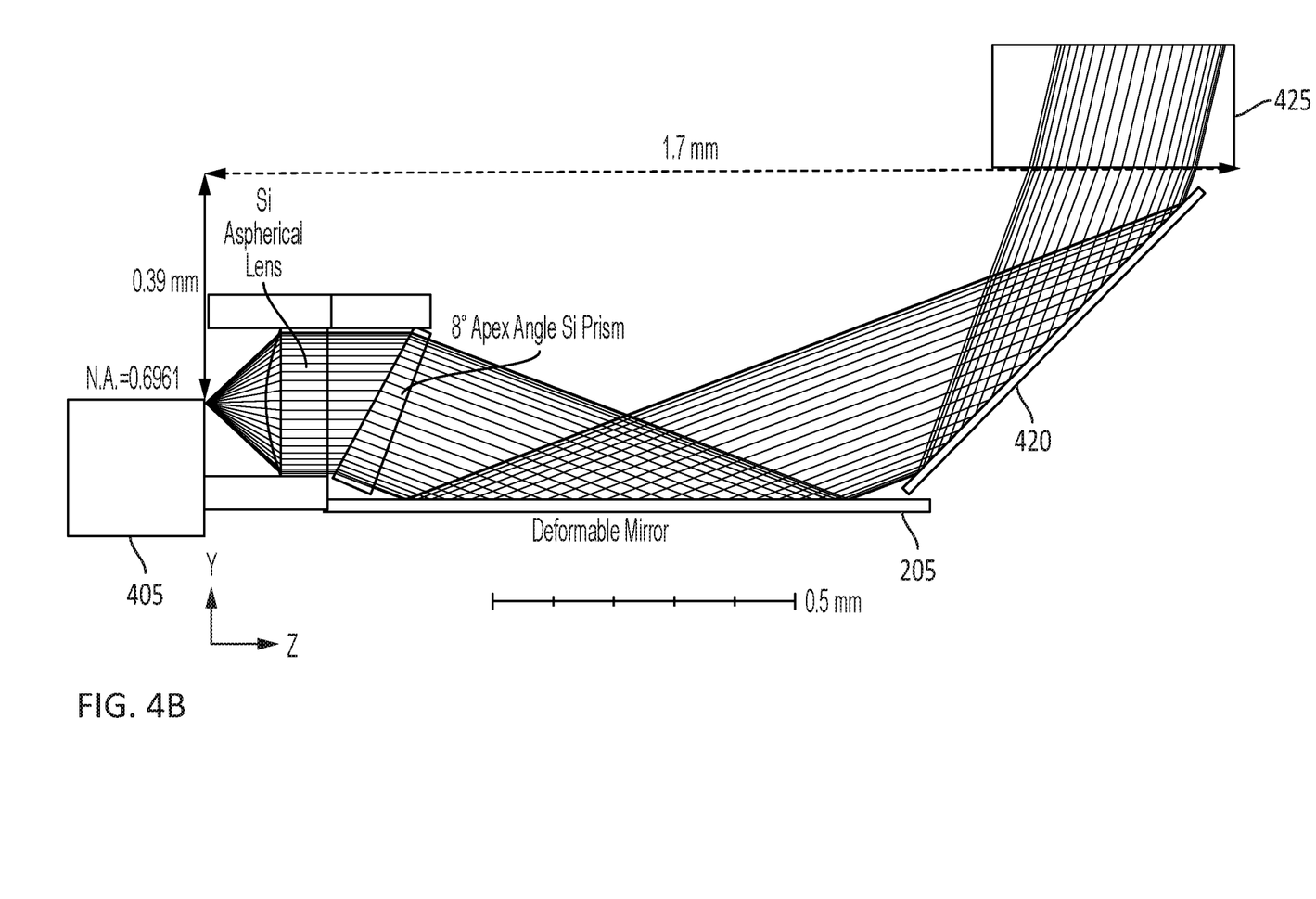
FIG. 4B is a side view of a portion of a spectrophotometer, according to an embodiment of the present disclosure. Each of FIGS. 3, 4A, and 4B is drawn to scale, for a respective embodiment.

FIGS. 4A and 4B show optical configurations employing the phase modulator for speckle mitigation 300 in the outgoing path (i.e. to apply phase modulation to the light from the light source 105 before the light interacts with the sample). At the left edge of each of FIGS. 4A and 4B, laser light at various wavelengths is coupled into free space out of the edge of a photonic integrated circuit (PIC) (e.g., a silicon PIC) 405 (e.g., out of a facet of a waveguide on the PIC 405, the facet being at the edge of the PIC 405). This light is collimated by an aspherical lens 410 (and, in the embodiment of FIG. 4B, is steered by a prism (e.g., a silicon prism)) and caused to reflect from the surface of the deformable membrane 205. The light then propagates (after, in the embodiment of FIG. 4B, reflecting from an additional mirror 420) through a window 425 (e.g., a fused silica window having a thickness of 0.2 mm and a diameter of 0.5 mm) toward the sample (e.g., toward the skin of a subject). In the embodiment of FIG. 4B, the launch point, at the edge of the PIC 405, may be at a height of about 0.163 mm above the surface of the deformable membrane 205; the angle of incidence at the window (labeled "X°" in FIG. 4A, and defined as the angle between the direction of propagation and a vector that is normal to the surface) may be between 5 degrees and 35 degrees, and the numerical aperture may be 0.22. In FIG. 4B, the angle of incidence for light reflecting from the deformable membrane 205 may be between 45 degrees and 80 degrees, the angle of incidence for light reflecting from the additional mirror 420 may be between 45 degrees and 80 degrees, and the angle of incidence at the window 425 may be between 5 degrees and 35 degrees. The angle of incidence on the hypotenuse side of the prism may be between 15 degrees and 45 degrees, and the angle of incidence on the leg side of the prism may be between 0 degrees and 10 degrees.

As used herein, "a portion of" something means "at least some of" the thing, and as such may mean less than all of, or all of, the thing. As such, "a portion of" a thing includes the entire thing as a special case, i.e., the entire thing is an example of a portion of the thing. As used herein, when a second quantity is "within Y" of a first quantity X, it means that the second quantity is at least X−Y and the second quantity is at most X+Y. As used herein, when a second number is "within Y %" of a first number, it means that the second number is at least (1−Y/100) times the first number and the second number is at most (1+Y/100) times the first number. As used herein, the word "or" is inclusive, so that, for example, "A or B" means any one of (i) A, (ii) B, and (iii) A and B.

The term "processing circuit" is used herein to mean any combination of hardware, firmware, and software, employed to process data or digital signals. Processing circuit hardware may include, for example, application specific integrated circuits (ASICs), general purpose or special purpose central processing units (CPUs), digital signal processors (DSPs), graphics processing units (GPUs), and programmable logic devices such as field programmable gate arrays (FPGAs). In a processing circuit, as used herein, each function is performed either by hardware configured, i.e., hard-wired, to perform that function, or by more general-purpose hardware, such as a CPU, configured to execute instructions stored in a non-transitory storage medium. A processing circuit may be fabricated on a single printed circuit board (PCB) or distributed over several interconnected PCBs. A processing circuit may contain other processing circuits; for example, a processing circuit may include two processing circuits, an FPGA and a CPU, interconnected on a PCB.

Spatially relative terms, such as "beneath", "below", "lower", "under", "above", "upper" and the like, may be used herein for ease of description to describe one element or feature's relationship to another element(s) or feature(s) as illustrated in the figures. It will be understood that such spatially relative terms are intended to encompass different orientations of the device in use or in operation, in addition to the orientation depicted in the figures. For example, if the device in the figures is turned over, elements described as "below" or "beneath" or "under" other elements or features would then be oriented "above" the other elements or features. Thus, the example terms "below" and "under" can encompass both an orientation of above and below. The device may be otherwise oriented (e.g., rotated 90 degrees or at other orientations) and the spatially relative descriptors used herein should be interpreted accordingly. In addition, it will also be understood that when a layer is referred to as being "between" two layers, it can be the only layer between the two layers, or one or more intervening layers may also be present.

The terminology used herein is for the purpose of describing particular embodiments only and is not intended to be limiting of the inventive concept. As used herein, the terms "substantially," "about," and similar terms are used as terms of approximation and not as terms of degree, and are intended to account for the inherent deviations in measured or calculated values that would be recognized by those of ordinary skill in the art.

As used herein, the term "major component" refers to a component that is present in a composition, polymer, or product in an amount greater than an amount of any other single component in the composition or product. In contrast, the term "primary component" refers to a component that makes up at least 50% by weight or more of the composition, polymer, or product. As used herein, the term "major portion", when applied to a plurality of items, means at least half of the items. As used herein, any structure or layer that is described as being "made of" or "composed of" a substance should be understood (i) in some embodiments, to contain that substance as the primary component or (ii) in some embodiments, to contain that substance as the major component.

It will be understood that when an element or layer is referred to as being "on", "connected to", "coupled to", or "adjacent to" another element or layer, it may be directly on, connected to, coupled to, or adjacent to the other element or layer, or one or more intervening elements or layers may be present. In contrast, when an element or layer is referred to as being "directly on", "directly connected to", "directly coupled to", or "immediately adjacent to" another element or layer, there are no intervening elements or layers present.

Any numerical range recited herein is intended to include all sub-ranges of the same numerical precision subsumed within the recited range. For example, a range of "1.0 to 10.0" or "between 1.0 and 10.0" is intended to include all subranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Similarly, a range described as "within 35% of 10" is intended to include all subranges between (and including) the recited minimum value of 6.5 (i.e., (1−35/100) times 10) and the recited maximum value of 13.5 (i.e., (1+35/100) times 10), that is, having a minimum value equal to or greater than 6.5 and a maximum value equal to or less than 13.5, such as, for example, 7.4 to 10.6. Any maximum numerical limitation recited herein is intended to include all lower numerical limitations subsumed therein and any minimum numerical limitation recited in this specification is intended to include all higher numerical limitations subsumed therein.

Although exemplary embodiments of a deformable membrane for speckle mitigation have been specifically described and illustrated herein, many modifications and variations will be apparent to those skilled in the art. Accordingly, it is to be understood that a deformable membrane for speckle mitigation constructed according to principles of this disclosure may be embodied other than as specifically described herein. The invention is also defined in the following claims, and equivalents thereof.

What is claimed is:

1. A system, comprising:
   a laser for producing laser light;
   a photodetector for detecting the laser light after interaction of the laser light with a sample; and
   a phase modulator, comprising:
   a single monolithic layer comprising:
   a silicon deformable membrane, for modulating the phase of the laser light; and
   a membrane frame supporting the silicon deformable membrane, and
   a piezoelectric actuator monolithically integrated with the single monolithic layer and configured to vibrate the silicon deformable membrane,
   wherein the membrane frame has a thickness equal to at least twice a thickness of the silicon deformable membrane.

2. The system of claim 1, wherein the silicon deformable membrane is configured to modulate the phase of the laser light before the interaction of the laser light with the sample.

3. The system of claim 1, wherein the silicon deformable membrane is configured to modulate the phase of the laser light after the interaction of the laser light with the sample.

4. The system of claim 1, wherein the system is configured to cause the laser light to reflect from the silicon deformable membrane.

5. The system of claim 1, wherein the system is configured to cause the laser light to be transmitted through the silicon deformable membrane.

6. The system of claim 1, wherein the silicon deformable membrane has a thickness of at least 0.5 microns.

7. The system of claim 1, wherein the silicon deformable membrane has a thickness of at most 5 microns.

8. The system of claim 1, wherein the membrane frame has a thickness at most 50 times the thickness of the silicon deformable membrane.

9. The system of claim 1, wherein the membrane frame surrounds the silicon deformable membrane.

10. The system of claim 9, further comprising a transition region inside the membrane frame and surrounding the silicon deformable membrane, the transition region having a thickness greater than that of the silicon deformable membrane and less than that of the membrane frame.

11. The system of claim 9, wherein the perimeter of the silicon deformable membrane has a curvilinear shape.

12. The system of claim 1, further comprising an actuator frame supporting the membrane frame.

13. The system of claim 12, wherein the actuator frame has a thickness of at least 50 microns.

14. The system of claim 13, wherein the piezoelectric actuator is a cantilevered piezoelectric actuator.

15. The system of claim 13, wherein the single monolithic layer comprises the actuator frame.

16. The system of claim 15, wherein the piezoelectric actuator is on a shelf at one end of the actuator frame, and the shelf is connected to the membrane frame by a first tab.

17. The system of claim 16, wherein the silicon deformable membrane is connected to the actuator frame by a second tab, opposite the first tab.

18. The system of claim 15, wherein the membrane frame has a thickness at most 50 times the thickness of the silicon deformable membrane.

* * * * *